United States Patent
Buchnik et al.

(10) Patent No.: US 12,070,264 B2
(45) Date of Patent: Aug. 27, 2024

(54) ACCURATE TISSUE PROXIMITY

(71) Applicant: BIOSENSE WEBSTER (ISRAEL) LTD., Yokneam (IL)

(72) Inventors: Yael Buchnik, Adi (IL); Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 213 days.

(21) Appl. No.: 17/383,511

(22) Filed: Jul. 23, 2021

(65) Prior Publication Data
US 2023/0028867 A1 Jan. 26, 2023

(51) Int. Cl.
*A61B 18/14* (2006.01)
*A61B 18/00* (2006.01)

(52) U.S. Cl.
CPC ...... *A61B 18/1492* (2013.01); *A61B 2018/00773* (2013.01); *A61B 2018/1467* (2013.01); *A61B 2562/0223* (2013.01); *A61B 2562/0257* (2013.01)

(58) Field of Classification Search
CPC ...... A61B 18/1492; A61B 2018/00773; A61B 2018/1467; A61B 2562/0223; A61B 2562/0257
See application file for complete search history.

(56) References Cited

U.S. PATENT DOCUMENTS

| | | | |
|---|---|---|---|
| 2,285,342 A | 6/1942 | Maclellan | |
| 5,078,714 A | 1/1992 | Katims | |
| 5,341,807 A | 8/1994 | Nardella | |
| 5,391,199 A | 2/1995 | Ben Haim | |
| 5,447,529 A | 9/1995 | Marchlinski | |
| 5,469,857 A | 11/1995 | Laurent | |
| 5,662,108 A | 9/1997 | Budd | |
| 5,673,704 A | 10/1997 | Marchlinski | |
| 5,836,874 A | 11/1998 | Swanson | |
| 5,836,990 A | 11/1998 | Li | |
| 5,891,095 A | 4/1999 | Eggers | |
| 5,935,079 A | 8/1999 | Swanson | |
| 6,239,724 B1 | 5/2001 | Doron | |
| 6,332,089 B1 | 12/2001 | Acker | |
| 6,484,118 B1 | 11/2002 | Govari | |
| 6,618,612 B1 | 9/2003 | Acker | |
| 6,690,963 B2 | 2/2004 | Ben Haim | |

(Continued)

FOREIGN PATENT DOCUMENTS

| EP | 1767166 A1 | 3/2007 | |
|---|---|---|---|
| EP | 3498162 A1 * | 6/2019 | ............. A61B 18/12 |

(Continued)

OTHER PUBLICATIONS

European Search report for corresponding EPA No. 22186415.0 dated Dec. 6, 2022.

*Primary Examiner* — Linda C Dvorak
*Assistant Examiner* — Abigail Bock

(57) ABSTRACT

A medical system includes a catheter configured to be inserted into a body part of a living subject, and including a distal end comprising an electrode, and a processor configured to compute position coordinates of the electrode, and find a measure of proximity of the electrode to tissue of the body part responsively to the position coordinates of the electrode and position coordinates of a wall of an anatomical map of the body part.

6 Claims, 4 Drawing Sheets

(56) References Cited

U.S. PATENT DOCUMENTS

| | | |
|---|---|---|
| 10,835,207 B2 | 11/2020 | Altmann |
| 2002/0065455 A1 | 5/2002 | Ben Haim |
| 2003/0120150 A1 | 6/2003 | Govari |
| 2004/0068178 A1 | 4/2004 | Govari |

FOREIGN PATENT DOCUMENTS

| | | |
|---|---|---|
| EP | 3498162 A1 | 6/2019 |
| EP | 3785612 A1 | 3/2021 |
| WO | WO1996005768 A1 | 2/1996 |

* cited by examiner

ACCURATE TISSUE PROXIMITY

FIELD OF THE INVENTION

The present invention relates to medical devices, and in particular, but not exclusively to, catheter electrodes.

BACKGROUND

A wide range of medical procedures involve placing probes, such as catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,690,963, 6,484,118, 6,239,724, 6,618,612 and 6,332,089, in PCT International Publication No. WO 1996/005768, and in U.S. Patent Application Publications Nos. 2002/0065455 and 2003/0120150 and 2004/0068178. Locations may also be tracked using impedance or current based systems.

One medical procedure in which these types of probes or catheters have proved extremely useful is in the treatment of cardiac arrhythmias. Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure, mapping followed by ablation, electrical activity at points within the heart is typically sensed and measured by advancing a catheter containing one or more electrical sensors into the heart, and acquiring data at a multiplicity of points. These data are then utilized to select the endocardial target areas at which the ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral vein, and then guided into the chamber of the heart of concern. A typical ablation procedure involves the insertion of a catheter having a one or more electrodes at its distal end into a heart chamber. A reference electrode may be provided, generally taped to the skin of the patient or by means of a second catheter that is positioned in or near the heart. RF (radio frequency) current is applied through the tip electrode(s) of the ablating catheter, and current flows through the media that surrounds it, i.e., blood and tissue, between the tip electrode(s) and an indifferent electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive.

Therefore, when placing an ablation or other catheter within the body, particularly near the endocardial tissue, it is desirable to have the distal tip of the catheter in direct contact with the tissue. The contact can be verified, for example, by measuring the contact between the distal tip and the body tissue. U.S. Patent Application Publication Nos. 2007/0100332, 2009/0093806 and 2009/0138007, describe methods of sensing contact pressure between the distal tip of a catheter and tissue in a body cavity using a force sensor embedded in the catheter.

A number of references have reported methods to determine electrode-tissue contact, including U.S. Pat. Nos. 5,935,079; 5,891,095; 5,836,990; 5,836,874; 5,673,704; 5,662,108; 5,469,857; 5,447,529; 5,341,807; 5,078,714; and Canadian Patent Application 2,285,342. A number of these references, e.g., U.S. Pat. Nos. 5,935,079, 5,836,990, and 5,447,529 determine electrode-tissue contact by measuring the impedance between the tip electrode and a return electrode. As disclosed in the '529 patent, it is generally known than impedance through blood is generally lower that impedance through tissue. Accordingly, tissue contact has been detected by comparing the impedance values across a set of electrodes to premeasured impedance values when an electrode is known to be in contact with tissue and when it is known to be in contact only with blood.

SUMMARY

There is provided in accordance with an embodiment of the present invention, a medical system, including a catheter configured to be inserted into a body part of a living subject, and including a distal end including an electrode, and a processor configured to compute position coordinates of the electrode, and find a measure of proximity of the electrode to tissue of the body part responsively to the position coordinates of the electrode and position coordinates of a wall of an anatomical map of the body part.

Further in accordance with an embodiment of the present invention, the system includes a display, wherein the processor is configured to render to the display a representation of the catheter, and provide an indication of the measure of proximity of the electrode to the tissue on the representation of the catheter.

Still further in accordance with an embodiment of the present invention the processor is configured to render to the display the anatomical map with the representation of the catheter disposed inside the anatomical map.

Additionally in accordance with an embodiment of the present invention the catheter includes a magnetic sensor, the system further includes at least one magnetic generator coil configured to transmit alternating magnetic fields into a region in which the body part is located, and generate electrical signals in the magnetic sensor indicative of a position and orientation of the magnetic sensor, and the processor is configured to compute the position coordinates of the electrode responsively to the electrical signals.

Moreover, in accordance with an embodiment of the present invention the processor is configured to compute the position and orientation of the magnetic sensor responsively to the electrical signals, and compute the position coordinates of the electrode responsively to the computed position and orientation of the magnetic sensor and a given spatial relationship between the magnetic sensor and the electrode.

Further in accordance with an embodiment of the present invention the catheter includes a distal end assembly and multiple electrodes disposed on the distal end assembly, the processor is configured to compute respective position coordinates of the multiple electrodes, and find respective measures of proximity of the multiple electrodes to tissue of the body part responsively to the respective position coordinates of the multiple electrodes and the position coordinates of the wall of the anatomical map of the body part.

Still further in accordance with an embodiment of the present invention, the system includes a display, wherein the processor is configured to render to the display a representation of the catheter, and provide respective indications of the respective measures of proximity of respective ones of the electrodes to the tissue on the representation of the catheter.

Additionally, in accordance with an embodiment of the present invention the processor is configured to render to the display the anatomical map with the representation of the catheter disposed inside the anatomical map.

Moreover in accordance with an embodiment of the present invention the catheter includes a magnetic sensor, the system further includes at least one magnetic generator coil configured to transmit alternating magnetic fields into a region in which the body part is located, and generate electrical signals in the magnetic sensor indicative of a position and orientation of the magnetic sensor, and the processor is configured to compute the respective position coordinates of the multiple electrodes responsively to the electrical signals.

Further in accordance with an embodiment of the present invention the processor is configured to compute the position and orientation of the magnetic sensor responsively to the electrical signals, and compute the respective position coordinates of the multiple electrodes responsively to the computed position and orientation of the magnetic sensor and a given spatial relationship between the magnetic sensor and the multiple electrodes.

There is also provided in accordance with another embodiment of the present invention, a medical method, including computing position coordinates of an electrode disposed on a distal end of a catheter inserted into a body part of a living subject, and finding a measure of proximity of the electrode to tissue of the body part responsively to the position coordinates of the electrode and position coordinates of a wall of an anatomical map of the body part.

Still further in accordance with an embodiment of the present invention, the method includes rendering to a display a representation of the catheter, and providing an indication of the measure of proximity of the electrode to the tissue on the representation of the catheter.

Additionally, in accordance with an embodiment of the present invention, the method includes rendering to the display the anatomical map with the representation of the catheter disposed inside the anatomical map.

Moreover, in accordance with an embodiment of the present invention, the method includes transmitting alternating magnetic fields into a region in which the body part is located generating electrical signals in a magnetic sensor of the catheter indicative of a position and orientation of the magnetic sensor, and wherein the computing includes computing the position coordinates of the electrode responsively to the electrical signals.

Further in accordance with an embodiment of the present invention, the method includes computing the position and orientation of the magnetic sensor responsively to the electrical signals, and wherein the computing the position coordinates includes computing the position coordinates of the electrode responsively to the computed position and orientation of the magnetic sensor and a given spatial relationship between the magnetic sensor and the electrode.

Still further in accordance with an embodiment of the present invention, the method includes computing respective position coordinates of multiple electrodes disposed on a distal end assembly of the catheter, and finding respective measures of proximity of the multiple electrodes to tissue of the body part responsively to the respective position coordinates of the multiple electrodes and the position coordinates of the wall of the anatomical map of the body part.

Additionally, in accordance with an embodiment of the present invention, the method includes rendering to a display a representation of the catheter, and providing respective indications of the respective measures of proximity of respective ones of the electrodes to the tissue on the representation of the catheter.

Moreover, in accordance with an embodiment of the present invention, the method includes rendering to the display the anatomical map with the representation of the catheter disposed inside the anatomical map.

Further in accordance with an embodiment of the present invention, the method includes transmitting alternating magnetic fields into a region in which the body part is located generating electrical signals in a magnetic sensor of the catheter indicative of a position and orientation of the magnetic sensor, and wherein the computing the respective position coordinates includes computing the respective position coordinates of the multiple electrodes responsively to the electrical signals.

Still further in accordance with an embodiment of the present invention, the method includes computing the position and orientation of the magnetic sensor responsively to the electrical signals, and wherein the computing the respective position coordinates includes computing the respective position coordinates of the multiple electrodes responsively to the computed position and orientation of the magnetic sensor and a given spatial relationship between the magnetic sensor and the multiple electrodes.

There is also provided in accordance with still another embodiment of the present invention, a software product, including a non-transient computer-readable medium in which program instructions are stored, which instructions, when read by a central processing unit (CPU), cause the CPU to compute position coordinates of an electrode disposed on a distal end of a catheter inserted into a body part of a living subject, and find a measure of proximity of the electrode to tissue of the body part responsively to the position coordinates of the electrode and position coordinates of a wall of an anatomical map of the body part.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
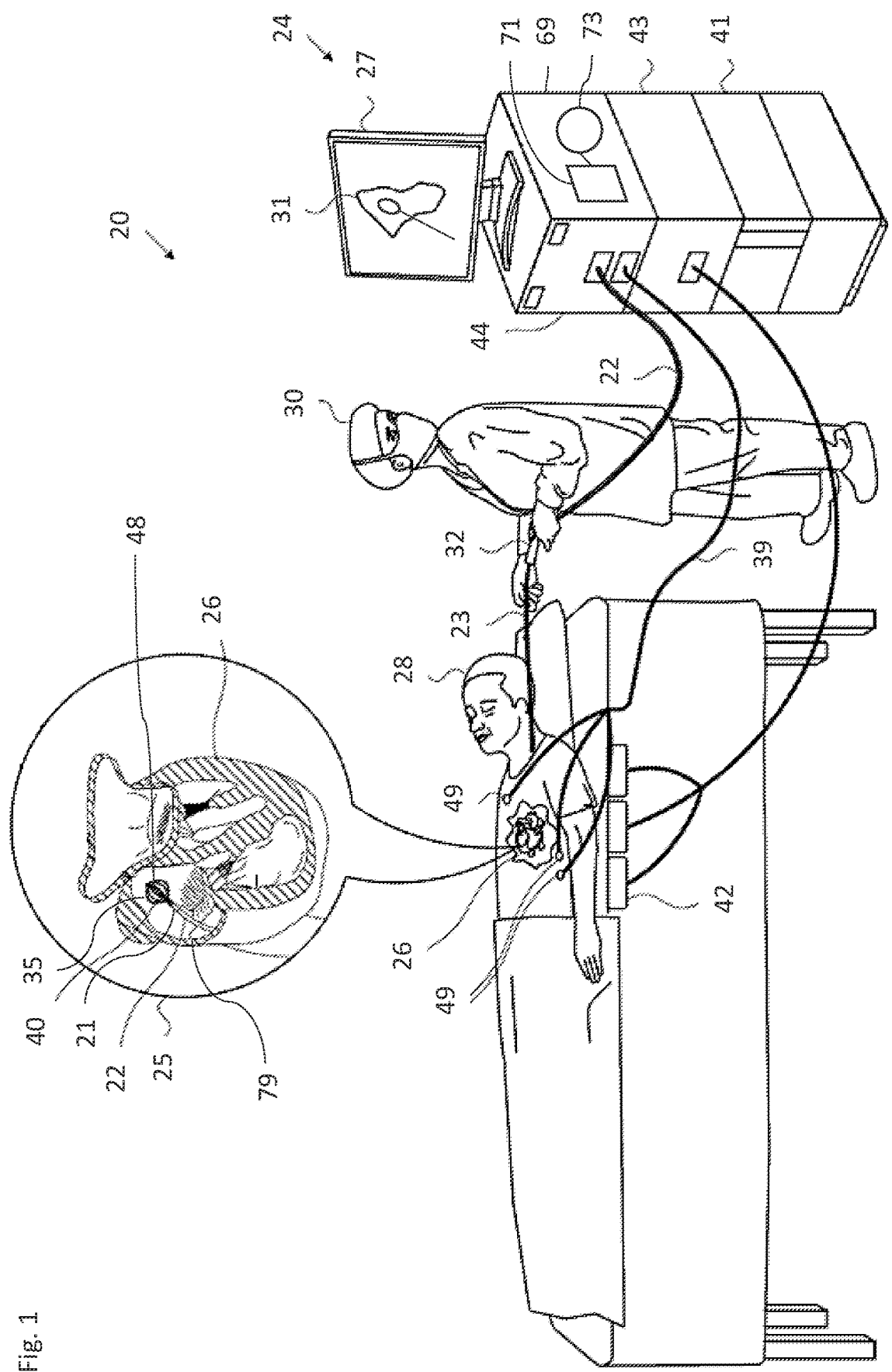
FIG. 1 is a schematic view of a medical system constructed and operative in accordance with an exemplary embodiment of the present invention.

As mentioned previously, in a two-step procedure, mapping followed by ablation, electrical activity at points within the heart is typically sensed and measured by advancing a catheter containing one or more electrodes into the heart, and acquiring data at a multiplicity of points. These data are then utilized to select the target areas at which the ablation is to be performed.

In particular, the electrical activity may be displayed as intracardial electrogram (IEGM) traces for analysis by a physician in order to find sources of arrhythmia. A catheter electrode, which is not in contact with tissue in the heart, generally measures some electrical signal from the heart tissue and a far field signal. When the catheter electrode is in contact with the heart tissue, the amplitude of the signal is mainly based on tissue conductivity, while the far field is minor. Therefore, the physician is generally interested in analyzing the IEGM traces of electrodes in contact with the tissue.

For focal catheters with one or two electrodes, a single IEGM trace is typically displayed for a physician to analyze. A physician can quickly determine based on the form of the signal whether the catheter electrode providing the signal is in contact with the tissue. However, multi-electrode catheters simultaneously capturing electrical activity from different tissue locations may provide data for a plurality of IEGM traces to be displayed at the same time on a single display. In some cases, the number of IEGM traces may be too numerous for the physician to easily determine which of the IEGM traces are provided by electrodes in contact with the tissue, and which are not.

An example of a multielectrode catheter is the Octaray® catheter, with in excess of 48 electrodes, produced by Biosense Webster Inc., of Irvine, CA, USA. The Octaray includes eight deflectable arms disposed at the distal end of a shaft, with each of the deflectable arms including six electrodes. Some catheters such as basket catheters may include more electrodes, for example, but not limited to, 120 electrodes.

In addition of the need to determine electrode contact during mapping discussed above, the physician performing an ablation procedure monitors the contact of electrodes with tissue, as effective ablation generally requires sufficient contact between the ablation electrode(s) and the tissue. For small numbers of electrodes, monitoring the contact may be performed by presenting a measure of the contact, such as the impedance seen by an electrode or the force on the electrode, numerically or even graphically. However, as the number of active electrodes used in an ablation procedure increases, it becomes increasingly difficult for the physician to monitor any parameter for the individual electrodes. In the case of electrode contact, this problem is exacerbated by the fact that in most cases as the contact varies, so the parameter measuring the contact also varies.

One solution is to try to view the proximity of the catheter electrodes within an anatomical map. However, simply viewing a representation of a catheter in an anatomical map does not easily allow the physician to see which electrodes of the catheter are close to, or in contact with, the tissue.

Embodiments of the present invention solve the above problems during a medical procedure such as a mapping or ablation procedure by providing a user interface in which the user views a representation of the catheter and its electrodes in an anatomical map. The proximity of the electrodes to tissue of the body part (e.g., heart) may be computed based on computing position coordinates of the electrodes and finding the distance (e.g., closest distance) of each of the electrodes to the wall of the anatomical map based on known position coordinates of the wall of the anatomical map. A measure of proximity of the electrodes to the tissue may be indicated on the respective electrodes using shading or coloring or any suitable indication. In some embodiments, only those electrodes in sufficient proximity to the tissue are indicated. In other embodiments, the indications used are dependent on the level of proximity of respective electrodes to the tissue. For example, different colors, and/or shadings, and/or brightness may be used to indicate different measures of proximity.

In disclosed embodiments, the position coordinates of the electrodes may be computed using magnetic position tracking which provides accurate results for the position coordinates. In some embodiments, the catheter includes a magnetic position sensor. Magnetic generator coils transmit alternating magnetic fields into a region where the body-part is located. The transmitted alternating magnetic fields generate signals in the magnetic sensor indicative of position and orientation of the magnetic sensor. The generated signals are transmitted to a processor, which computes the position and orientation of the magnetic sensor. Assuming the electrodes are arranged in a fixed spatial relationship with the magnetic sensor (for example, with a basket catheter, or grid-shaped catheter, or lasso-shaped catheter), the position coordinates of each the electrodes may be computed based on the position and orientation of the magnetic sensor and the fixed spatial relationship.

System Description

Reference is now made to FIG. 1, which is a schematic view of a medical system 20 constructed and operative in accordance with an exemplary embodiment of the present invention. The system 20 includes a catheter 40 configured to be inserted into a body part of a living subject (e.g., a patient 28). A physician 30 navigates the catheter 40 (for example, a basket catheter produced Biosense Webster, Inc. of Irvine, CA, USA), to a target location in a heart 26 of the patient 28, by manipulating an elongated deflectable element 22 of the catheter 40, using a manipulator 32 near a proximal end of the catheter 40, and/or deflection from a sheath 23. In the pictured embodiment, physician 30 uses catheter 40 to perform electro-anatomical mapping of a cardiac chamber and ablation of cardiac tissue.

Catheter 40 includes an expandable distal end assembly 35 (e.g., a basket assembly), which is inserted in a folded configuration, through sheath 23, and only after the catheter 40 exits sheath 23 does the distal end assembly 35 regain its intended functional shape. By containing distal end assembly 35 in a folded configuration, sheath 23 also serves to minimize vascular trauma on its way to the target location.

Catheter 40 includes a plurality of electrodes 48 (inset 25) disposed on the expandable distal end assembly 35 for sensing electrical activity and/or applying ablation power to ablate tissue of the body part. The catheter 40 may also include a proximal electrode 21 disposed on the deflectable element 22 proximal to the expandable distal end assembly 35. Catheter 40 may incorporate a magnetic position sensor (not shown) at the distal edge of deflectable element 22 (i.e., at the proximal edge of the distal end assembly 35). Typically, although not necessarily, the magnetic sensor is a Single-Axis Sensor (SAS). A second magnetic sensor (not shown) may be included at any suitable position on the assembly 35. The second magnetic sensor may be a Triple-Axis Sensor (TAS) or a Dual-Axis Sensor (DAS), or a SAS by way of example only, based for example on sizing considerations. The magnetic sensors, the proximal electrode 21, and electrodes 48 disposed on the assembly 35 are connected by wires running through deflectable element 22 to various driver circuitries in a console 24.

In some embodiments, system 20 comprises a magnetic-sensing sub-system to estimate an ellipticity of the basket assembly 35 of catheter 40, as well as its elongation/retraction state, inside a cardiac chamber of heart 26 by estimating the elongation of the basket assembly 35 from the distance between the magnetic sensors. Patient 28 is placed in a magnetic field generated by a pad containing one or more magnetic field generator coils 42, which are driven by a unit 43. The magnetic fields generated by coil(s) 42 transmit alternating magnetic fields into a region where the body-part is located. The transmitted alternating magnetic fields generate signals in the magnetic sensors, which are indicative of position and/or direction. The generated signals are transmitted to console 24 and become corresponding electrical inputs to a processor 41.

The method of position and/or direction sensing using external magnetic fields and magnetic sensors, is implemented in various medical applications, for example, in the CARTO® system, produced by Biosense-Webster, and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publication Nos. 2002/0065455 A1, 2003/0120150 A1 and 2004/0068178 A1.

Processor 41, typically part of a general-purpose computer, is further connected via a suitable front end and interface circuits 44, to receive signals from body surface-electrodes 49. Processor 41 is connected to body surface-electrodes 49 by wires running through a cable 39 to the chest of patient 28.

In an exemplary embodiment, processor 41 renders to a display 27, a representation 31 of at least a part of the catheter 40 and a mapped body-part (e.g., anatomical or electro-anatomical map), responsively to computed position coordinates of the catheter 40.

Processor 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

The medical system 20 may also include an ablation power generator 69 (such as an RF signal generator) configured to be connected to the catheter 40, and apply an electrical signal between one or more of the electrodes 48 and the proximal electrode 21. The medical system 20 may also include an irrigation reservoir 71 configured to store irrigation fluid, and a pump 73 configured to be connected to the irrigation reservoir 71 and the catheter 40, and to pump the irrigation fluid from the irrigation reservoir 71 via an irrigation tube through irrigation holes of the catheter 40.

The example illustration shown in FIG. 1 is chosen purely for the sake of conceptual clarity. FIG. 1 shows only elements related to the disclosed techniques for the sake of simplicity and clarity. System 20 typically comprises additional modules and elements that are not directly related to the disclosed techniques, and thus are intentionally omitted from FIG. 1 and from the corresponding description. The elements of system 20 and the methods described herein may be further applied, for example, to control an ablation of tissue of heart 26.

The catheter 40 has been described herein as a basket catheter. The expandable distal end assembly 35 may include any suitable number of splines, any suitable number of electrodes, and any suitable number of electrodes per spline. The catheter 40 may be implemented as any suitable catheter-type, for example, a balloon catheter, a lasso-shape catheter, a grid-shape catheter, or a flexible spline catheter where distal ends of flexible splines are not connected together.

Figure 2:
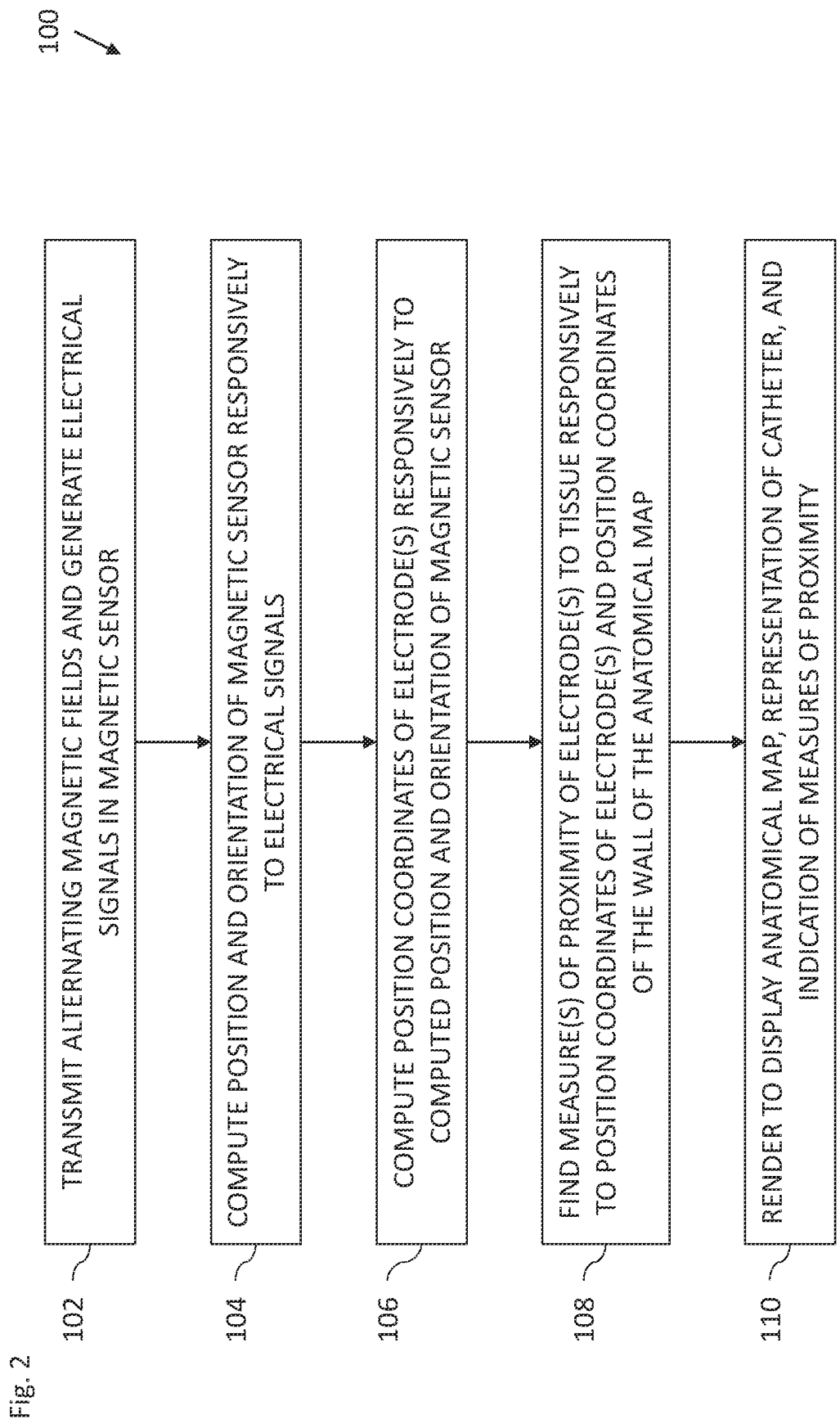
FIG. 2 is a flowchart including steps in a method of operation of the system of FIG. 1.
Figure 3:
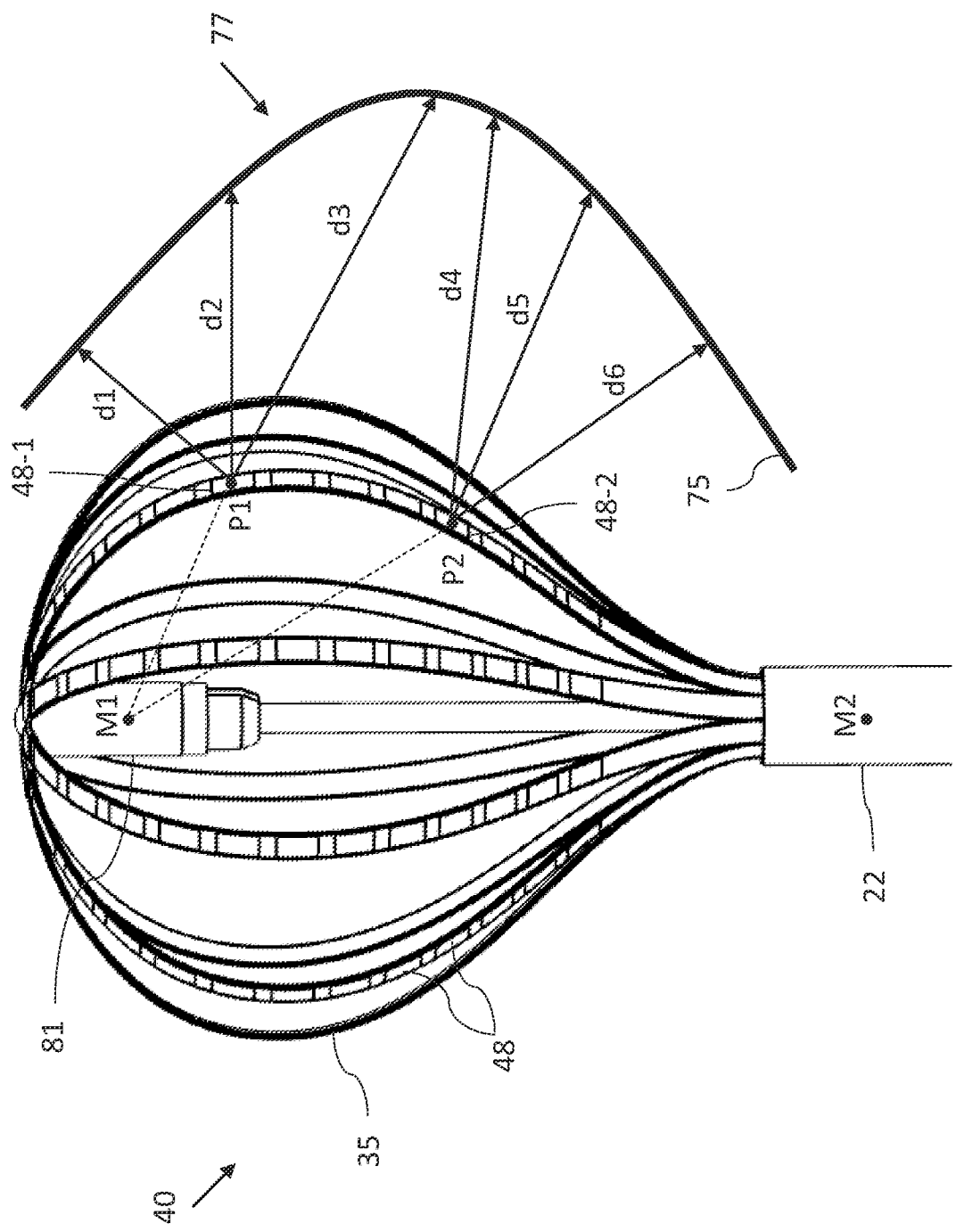
FIG. 3 is a schematic view of a catheter and a wall of an anatomical map used to illustrate finding measures of proximity of electrodes to tissue.

Reference is now made to FIG. 2, which is a flowchart 100 including steps in a method of operation of the system 20 of FIG. 1. Reference is also made to FIG. 3, which is a schematic view of the catheter 40 and a wall 75 of an anatomical map 77 used to illustrate finding measures of proximity of electrodes 48 (only some are labeled for the sake of simplicity) to tissue 79 (FIG. 1) of a body part (e.g., the heart 26 of FIG. 1).

The catheter 40 includes a magnetic sensor 81. In the example of FIG. 2, the magnetic sensor 81 is shown as being disposed in the expandable distal end assembly 35 towards the distal end of the expandable distal end assembly 35 centered at position M1. The magnetic sensor 81 may be disposed at any suitable position on the catheter 40, for example, at the distal end of the elongated deflectable element 22 centered at position M2. The catheter 40 may include two magnetic sensors 81, one positioned with its center at M1, and one positioned with its center at M2. The magnetic sensor 81 may include a SAS, DAS, or TAS, for example.

The catheter 40 described with reference to FIG. 3 includes the expandable distal end assembly 35 with multiple electrodes 48. In some embodiments, the catheter 40 may be replaced with a catheter which does not include expandable distal end assembly 35. In some embodiments, the catheter 40 may include one mapping and/or one ablation electrode.

The magnetic field generator coil(s) 42 (FIG. 1) are configured to: transmit (block 102) alternating magnetic fields into a region in which the body part is located and generate electrical signals in the magnetic sensor 81 indicative of a position and orientation of the magnetic sensor 81. The processor 41 is configured to compute (block 104) the position and orientation of the magnetic sensor 81 responsively to the electrical signals. As previously mentioned, the method of position and/or direction sensing using external magnetic fields and magnetic sensors, is implemented in various medical applications, for example, in the CARTO® system, produced by Biosense-Webster, and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publication Nos. 2002/0065455 A1, 2003/0120150 A1 and 2004/0068178 A1.

The processor 41 is configured to compute (block 106) the respective position coordinates of the electrodes 48 responsively to electrical signals. In some embodiments, the step of block 106 includes the processor 41 being configured to compute the respective position coordinates of the electrodes 48 responsively to the computed position and orientation of the magnetic sensor 81, and a given spatial relationship between the magnetic sensor 81 and the electrodes 48. For example, the position M1 of the magnetic sensor 81 is first determined in the step of block 104 and based on the given spatial relationship between M1 and electrode 48-1, the position P1 of electrode 48-1 may be determined. Similarly, the position P2 of electrode 48-2 may be determined. The given spatial relationship between the position and orientation of the magnetic sensor 81 and the positions of the electrodes 48 may be based on the expandable distal end assembly 35 having a generally stable shape once expanded. In some embodiments, the positions of the electrodes 48 with respect to the magnetic sensor 81 may depend on a level of expansion of the expandable distal end assembly 35. In some embodiments, the shape of the expandable distal end assembly 35 and therefore the positions of the electrodes 48 with respect to the magnetic sensor 81 may be determined based on the distance between two magnetic sensor 81 centered at M1 and M2.

The processor 41 is configured to find (block 108) respective measures of proximity of the multiple electrodes 48 to tissue 79 (FIG. 1) of the body part (e.g., the heart 26 of FIG. 1) responsively to the respective position coordinates of the multiple electrodes 48 and the position coordinates of the wall 75 of the anatomical map 77 of the body part. The position coordinates of each of the electrodes 48 may be compared to the position coordinates of the wall 75 to find the shortest respective distances between the electrodes 48 and the wall 75.

For example, FIG. 3 shows the position P1 of electrode 48-1 being compared to various position coordinates of the wall 75 yielding distance d1, d2, and d3, with d1 being the shortest distance from P1 to wall 75. Similarly, FIG. 3 shows the position P2 of electrode 48-2 being compared to various position coordinates of the wall 75 yielding distance d4, d5, and d6, with d6 being the shortest distance from P2 to wall 75. Therefore, the measure of proximity of P1 to the tissue 79 may be found based on d1, and the measure of proximity of P2 to the tissue 79 may be found based on d6.

The measure of proximity may be expressed as a level (for example, level 1, 2, 3 etc., or "in contact" or "not in contact", or a distance measurement, for example in millimeters). By way of example, if the closest distance from the electrode 48-1 to the wall 75 is less than a first threshold, then the measure of proximity may equal 1, and if the closest distance from the electrode 48-1 to the wall 75 is less than a second threshold, then the measure of proximity may equal 2, and so on. By way of another example, if the closest distance from the electrode 48-1 to the wall 75 is greater than or equal to a given threshold, then the measure of proximity may equal "not in contact", and if the closest distance from the electrode 48-1 to the wall 75 is less than the given threshold, then the measure of proximity may equal "in contact". By way of further example, if the closest distance from the electrode 48-1 to the wall 75 is d1, then the measure of proximity may equal d1 (or d1 rounded up or down) or a fraction or multiple of d1.

The position coordinates of the wall 75 may be generated as part of a mapping or imaging process. The anatomical map 77 may be generated based on moving the catheter 40 around the body part (close to the tissue of the body part) and recording positions of the electrodes 48 over time. The anatomical map 77 may then be generated by creating a shell around the recorded electrode positions. Various algorithms may be used to reconstruct the outer surface of a volume based on a collection of interior points of this sort. For example, processor 41 may apply a ball-pivoting algorithm that is described in U.S. Pat. No. 6,968,299. This algorithm computes a triangle mesh interpolating a given point cloud by "rolling" a ball of a certain radius over the point cloud. The vertices of the triangles that are found in this way define the outer surface of the cloud.

By way of another example, US Patent Application Publication No. 2010/0168550 describes a system for constructing multiple modeled shells indicative of the geometry and/or volume of a heart chamber. The system is configured to collect a plurality of location data points as an electrode is swept within the chamber. Each of the collected data points has an associated measured cardiac phase at which such point was acquired. The system is configured to segregate the collected electrode locations into sets based on the phase. Each set is characterized by a particular, associated phase of its constituent electrode locations. The system is configured to generate, for each set, a respective shell model that will represent the chamber at the associated phase. The shells, once constructed, may be used for, or in connection with, a variety of diagnostic, mapping, and/or therapeutic procedures. The system is also configured to verify that the electrode is in contact with the heart tissue before using the collected data point in the shell construction (e.g., using a phase angle parameter to verify contact).

As another example, US Patent Application Publication No. 2006/0178587 describes systems and methods for calibrating calculations based on catheter-originated measurements. One embodiment comprises a method for calibrating volume calculations for a fluid-filled cavity, such as a heart chamber. In this method, a first catheter configured to measure electrical characteristics and a second catheter configured to measure geometric characteristics are inserted into a fluid-filled cavity. Electrical characteristics of the fluid-filled cavity are measured with the first catheter and geometric characteristics of the cavity are measured with the second catheter. A volume segment is determined based on the measured geometric characteristics of the cavity, and a corresponding volume segment is determined based on the measured electrical characteristics of the cavity. Because the geometric calculation of the volume is known to be more accurate, the volume calculation based on the electrical measurements is adjusted (calibrated) to match the geometric calculation.

By way of another example, U.S. Pat. No. 10,835,207 describes a method for three-dimensional (3D) mapping including acquiring a plurality of two-dimensional (2D) ultrasonic images of a cavity in a body of a living subject. The 2D images have different, respective positions in a 3D reference frame. In each of the 2D ultrasonic images, pixels corresponding to locations within an interior of the cavity are identified. The identified pixels from the plurality of the 2D images are registered in the 3D reference frame so as to define a volume corresponding to the interior of the cavity. An outer surface of the volume is reconstructed, representing an interior surface of the cavity.

Figure 4:
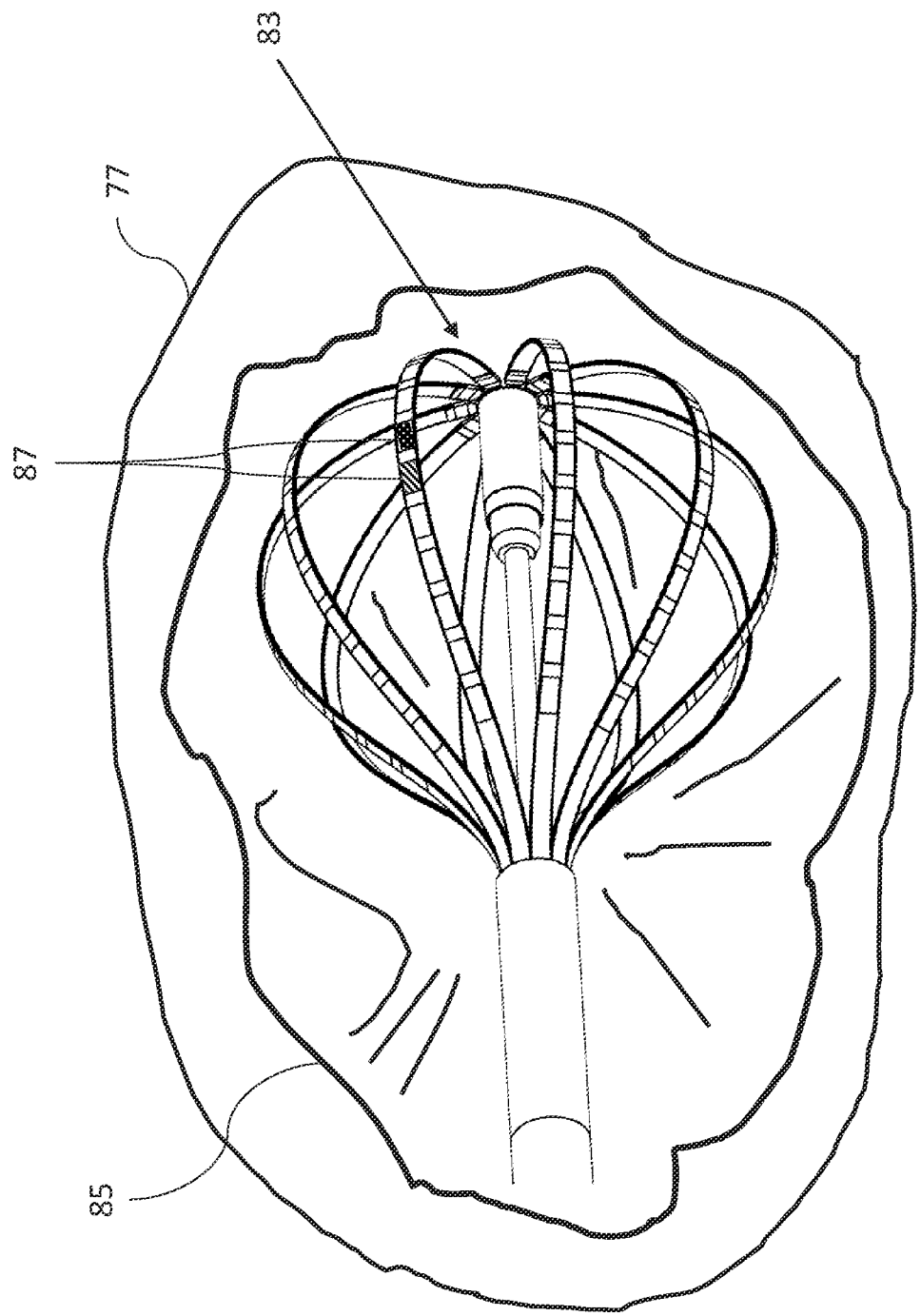
FIG. 4 is a schematic view showing a representation of the catheter of FIG. 3 inside the anatomical map.

Reference is now made to FIG. 4, which is a schematic view showing a representation 83 of the catheter 40 of FIG. 3 inside the anatomical map 77. Reference is also made to FIG. 2. The processor 41 (FIG. 1) is configured to render (block 110) to the display 27 (FIG. 1) the anatomical map 77 (which is shown with opening 85 for the sake of representation) with the representation 83 of the catheter 40 disposed inside the anatomical map 77. The processor 41 is configured to provide respective indications 87 of the respective measures of proximity of respective ones of the electrodes 48 (e.g., electrodes 48-1 and 48-2) (FIG. 3) to the tissue 79 (FIG. 1) on the representation 83 of the catheter 40. The indications 87 are shown as different levels of shading in the example of FIG. 4.

A measure of proximity of the electrodes 48 to the tissue 79 may be indicated on the respective electrodes using shading or coloring or another indication. In some embodiments, only those electrodes 48 in sufficient proximity to the tissue are provided with indications 87. In other embodiments, the indications 87 used are dependent on the respective measures of proximity of respective electrodes 48 to the tissue 79. For example, different colors, and/or, shadings, and/or brightness may be used to indicate different measures of proximity. As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g., "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and sub-combinations of the various features described hereinabove, as well as variations and modifications thereof which would occur to persons skilled in the art upon reading the foregoing description and which are not disclosed in the prior art.

What is claimed is:

1. A medical system, comprising:
   a catheter configured to be inserted into a heart of a living subject, and including a magnetic sensor and a distal end comprising a plurality of electrodes, where each of the electrodes has a predetermined spatial relationship relative to the magnetic sensor; and
   at least one magnetic generator coil configured to:
      transmit alternating magnetic fields into a region in which heart is located; and
      generate electrical signals in the magnetic sensor indicative of a position and orientation of the magnetic sensor; and
   a processor configured to:
   compute position coordinates of the electrodes responsively to the electrical signals; and
   find a measure of proximity of each of the electrodes to tissue of the heart responsively to the position coordinates of the electrodes and position coordinates of a wall of an anatomical map of the heart, wherein the anatomical map comprises a modeled shell of geometry of the heart; and
   a display, wherein the processor is configured to:
      render to the display a representation of the catheter and the plurality of electrodes upon the catheter; and
      provide indications of the measure of proximity of each of the electrodes to the nearest tissue of the heart, wherein the indications are provided upon the representation of the electrodes upon the catheter and wherein the indications comprise one or more of a brightness level, a shading, or a color where the brightness level, shading, or color indicates a level of proximity to the tissue selected from a plurality of levels, the levels including at least i) the electrode is not in contact with the tissue; and ii) the electrode is in contact with the tissue.

2. The medical system of claim 1, wherein the indications comprise a plurality of brightness levels where the brightness level of the electrodes indicates a closer proximity to the nearest tissue.

3. A medical method, comprising:
   computing position coordinates of a plurality of electrodes disposed on a distal end of a catheter inserted into a heart of a living subject responsively to electrical signals received from a magnetic sensor disposed on the catheter, wherein the catheter includes a magnetic sensor and a distal end comprising a plurality of electrodes, wherein each of the electrodes has a predetermined spatial relationship relative to the magnetic sensor, and wherein the electrical signals from the magnetic sensor are indicative of a position and orientation of the magnetic sensor;
   finding a measure of proximity of each the electrodes to tissue of the heart responsively to the position coordinates of the electrodes and position coordinates of a wall of an anatomical map of the heart, wherein the anatomical map comprises a modeled shell of geometry of the heart;
   rendering to a display a representation of the catheter and the plurality of electrodes upon the catheter; and
   providing indications of the measure of proximity of each of the electrodes to the nearest tissue of the heart, wherein the indications are provided upon the representation of the electrodes upon the catheter and wherein the indications comprise one or more of a brightness level, a shading, or a color where the brightness level, shading, or color indicates a level of proximity to the tissue selected from a plurality of levels, the levels including at least i) the electrode is not in contact with the tissue; and ii) the electrode is in contact with the tissue.

4. The medical method of claim 3, wherein the indications comprise a plurality of brightness levels where the brightness level of the electrodes indicates a closer proximity to the nearest tissue.

5. A software product, comprising a non-transient computer-readable medium in which program instructions are stored, which instructions, when read by a central processing unit (CPU), cause the CPU to:
   compute position coordinates of a plurality of electrodes disposed on a distal end of a catheter inserted into a heart of a living subject responsively to electrical signals received from a magnetic sensor disposed on the catheter, wherein the catheter includes a magnetic sensor and a distal end comprising a plurality of electrodes, where each of the electrodes has a predetermined spatial relationship relative to the magnetic sensor and wherein the electrical signals from the magnetic sensor are indicative of a position and orientation of the magnetic sensor; and
   find a measure of proximity of each the electrodes to tissue of the heart responsively to the position coordinates of the electrodes and position coordinates of a wall of an anatomical map of the heart;
   rendering to a display a representation of the catheter and the plurality of electrodes upon the catheter; and
   providing indications of the measure of proximity of each of the electrodes to the nearest tissue of the heart, wherein the indications are provided upon the representation of the electrodes upon the catheter and wherein the indications comprise one or more of a brightness level, a shading, or a color where the brightness level, shading, or color indicates a level of proximity to the tissue selected from a plurality of levels, the levels including at least i) the electrode is not in contact with the tissue; and ii) the electrode is in contact with the tissue.

6. The software product of claim 5, wherein the indications comprise a plurality of brightness levels where the brightness level of the electrodes indicates a closer proximity to the nearest tissue.

* * * * *